United States Patent [19]
Kenley et al.

[11] Patent Number: 6,044,691
[45] Date of Patent: Apr. 4, 2000

[54] BLOOD TUBING SET INTEGRITY TESTS FOR EXTRACORPOREAL CIRCUITS

[75] Inventors: Rodney S. Kenley, Libertyville; Seema A. Kapadia, Wheeling; Christine F. Schroeder, Gurnee; Thomas M. Feldsien, Island Lake, all of Ill.; Michael Duch, Charlottesville, Va.; Dennis M. Treu, Gurnee; Frederick H. Peter, Jr., Barrington, both of Ill.

[73] Assignee: Aksys, Ltd., Lincolnshire, Ill.

[21] Appl. No.: 09/140,483

[22] Filed: Aug. 26, 1998

[51] Int. Cl.[7] ...................................... B01D 61/30
[52] U.S. Cl. ......................... 73/40.5 R; 210/646
[58] Field of Search ................... 73/40.5 R, 40; 210/646, 741

[56] References Cited

U.S. PATENT DOCUMENTS

| | | | |
|---|---|---|---|
| 4,444,597 | 4/1984 | Gortz et al. | 134/18 |
| 4,449,392 | 5/1984 | Huscke . | |
| 4,526,574 | 7/1985 | Pekkarinen | 604/52 |
| 4,695,385 | 9/1987 | Boag . | |
| 4,834,888 | 5/1989 | Polaschegg . | |
| 5,580,460 | 12/1996 | Polaschegg | 210/646 |
| 5,591,344 | 1/1997 | Kenley et al. . | |
| 5,624,551 | 4/1997 | Baumann et al. | 210/134 |
| 5,674,390 | 10/1997 | Matthews et al. | 210/261 |

FOREIGN PATENT DOCUMENTS 3442744  6/1986  Germany .

OTHER PUBLICATIONS

W. Gentles, et al., Programmable Machine for Dialyzer Reuse, Med. & Bio. Eng. & Comp., vol. 18, pp. 765–781 (1980).

*Primary Examiner*—Hezron Williams
*Assistant Examiner*—Michael Cygan
*Attorney, Agent, or Firm*—McDonnell, Boehnen, Hulbert & Berghoff

[57] ABSTRACT

Several tests are described for verifying the integrity of the extracorporeal circuit of a medical instrument, such as a dialysis machine. One test verifies the condition of the blood tubing set. Another test verifies that the clamps in the arterial and venous lines adequately occlude the arterial and venous lines. Another test confirms that the arterial and venous lines are properly installed on their respective ports for receiving the lines after the treatment session has ended. In this last test, a fluid such as heated water is then introduced into one of the arterial or venous lines and sent out of the line through its respective port, where it is detected with suitable fluid detection equipment such as a thermistor. The heated fluid and thermistor verify that the arterial line is connected to its arterial port and the venous line is connected to its venous port and that there is an unobstructed fluid path in the blood tubing set. If the lines are installed on the wrong port, the user is prompted to correctly install the arterial and venous lines on their respective ports.

34 Claims, 5 Drawing Sheets

BLOOD TUBING SET INTEGRITY TESTS FOR EXTRACORPOREAL CIRCUITS

BACKGROUND OF THE INVENTION

A. Field of the Invention

This invention relates generally to medical instruments that have extracorporeal blood circuits, such as hemodialysis machines. More particularly, the invention relates to methods for testing the integrity of such circuits in advance of a treatment session so as to improve patient safety and reliable operation of the machine.

B. Description of Related Art

Various types of medical instruments, most notably artificial kidney and liver dialysis machines, incorporate extracorporeal circuits. The purpose of such extracorporeal circuits is generally to carry the blood from the patient, filter the blood, and return the blood to the patient. Most configurations of the extracorporeal circuit include a line designated "arterial" that connects to a fistula needle inserted into the patient's body. A blood pump segment is placed in the arterial line which, in conjunction with a blood pump in the instrument, pumps blood from the patient's body to a filtration apparatus. The filtration device is a dialyzer in the case of the artificial kidney machine. Blood is then returned to the patient by a second line, termed the "venous" line. Typically, clamps, bubble traps, pressure transducers, injection sites, and other components are included in the arterial or venous line, and serve various functions incident to operation of the machine and/or for purposes of patient safety.

To perform dialysis, the patient connects their arterial and venous fistula needles, or central venous catheters, to connectors terminating the arterial and venous lines of the extracorporeal circuit. When the dialysis session is completed, the patient disconnects the arterial and venous lines from the blood access devices. In some machines, the entire extracorporeal circuit is replaced with a new one for the next session with the machine. In other situations, the extracorporeal circuit is reused. In this latter situation, typically the arterial and venous line connectors are connected either to a disinfection manifold in fluid communication with a source of disinfection fluids, or to a separate reuse device, and the entire extracorporeal circuit is subject to cleaning and disinfection. See e.g., the patent to Kenley et al., U.S. Pat. No. 5,591,344, the patent to Boag, U.S. Pat. No. 4,695,385, and the German patent to Polaschegg, No. DE 3,442,744.

When the extracorporeal circuit is replaced after every use, there is generally less of a concern that the extracorporeal circuit may be defective, since quality assurance testing would generally be performed as an incident to manufacture of the extracorporeal circuit. However, in the case of reuse of the extracorporeal circuit, the need for subsequent integrity testing of the dialyzer and blood tubing set is more pronounced. This is because intervening processes involving the extracorporeal circuit, including the dialysis session, priming, cleaning, disinfection and so forth, present at least a small possibility that the condition of the extracorporeal circuit has been degraded from the condition it was in when it was new.

It is known in the art to test the condition of the dialyzer membrane prior to initiation of dialysis. Procedures for testing the integrity of the dialyzer membrane are described in the above-referenced Kenley et al. and Polaschegg patents, the U.S. Pat. No. 4,834,888 to Polaschegg; U.S. Pat. No. 4,449,392 to Huschke; U.S. Pat. No. 4,444,597 to Gortz, and in the article of W. Gentles et al., *Programmable Machine for Dialyzer Reuse*, Med. & Bio. Eng. & Comp., Vol. 18, pp. 765–781 (1980). Such tests include pressure tests for detecting leaks in the dialyzer membrane, and clearance tests for determining the capacity of the dialyzer membrane to remove toxins such as urea from the blood.

The present inventors have appreciated that testing the integrity of the dialyzer membrane in the manner known in the prior art overlooks other potential points of failure in the extracorporeal circuit. The inventors have devised methods for in situ testing the remainder of the extracorporeal circuit, including the clamps in the instrument which occlude the arterial and venous lines, the connectors at the end of the lines, adhesion points between the tubing and various rigid connectors, and the tubing itself.

Additionally, the inventors have appreciated that the connection of the arterial and venous line connectors to the disinfection manifold or reuse device is another point of potential failure during disinfection and cleaning operations. The inventors have developed methods for determining whether the arterial and venous lines have been installed on the proper ports of the disinfection manifold or reuse device (i.e., the arterial connector was installed in the "arterial port" and the venous line on the "venous port"). The inventors have also developed methods to determine that the connection is in fact a secure and tight connection such that leakage of fluid or air will not occur when disinfection, priming, and/or cleaning fluids are circulated through the ports, or when integrity testing as described herein is performed.

The result of these achievements is that patient safety and machine operations are both improved. The methods can be performed both on new extracorporeal circuits (i.e., before they are used for the first time in the machine), adding an additional measure of quality assurance, as well as on extracorporeal circuits that are subject to repeated reuse. Further, the advancements provided by the present invention are all the more noteworthy with the advent of dialysis therapy being performed outside of the conventional dialysis clinic environment, and with the more widespread acceptance of dialyzer reuse. In such applications, the integrity testing provided by the present invention gives extra measures of safety and assurances that treatments involving reusable extracorporeal blood circuits can be safely performed outside of conventional dialysis clinic and hospital settings, and in particular in the home, nursing home, and self-care clinic environments.

SUMMARY OF THE INVENTION

Several methods or tests are provided for testing the integrity of a blood tubing set for an extracorporeal circuit and its interaction with the rest of the instrument. The blood tubing set includes an arterial line and a venous line. The methods are performed in situ in a machine containing the blood tubing set, the machine having arterial and venous manifold ports for receiving the arterial and venous lines after the treatment session has ended. The manifold ports and arterial and venous lines are connected to hydraulic circuitry in the machine via one or more valves. When the valves are closed, they isolate the blood tubing set from the hydraulic circuitry. When the valves are opened, they allow fluid or air to pass through the lines and ports and into or out of the blood tubing set.

A tubing integrity test is specifically designed to test the condition of the arterial and venous lines of the extracorporeal circuit. This test may be performed independently of, or at the same time as, a test of the dialyzer or other filter apparatus in the extracorporeal circuit. The test includes a first step of connecting the arterial and venous lines to the arterial and venous manifold ports. Then, any fluid which may be present in the blood tubing set is evacuated from the blood tubing set. This step involves the steps of opening the arterial and venous pinch clamps located on the instrument through which the tubing is threaded and introducing air into the arterial and venous lines to push fluid out of the extracorporeal circuit through the one or more valves. The air may come from an air pump connected to a vent line above the venous bubble trap.

Then, the blood tubing set is isolated from the hydraulic circuitry in the machine by closing the one or more valves. Air is forced into the blood tubing set so as to raise the pressure in the blood tubing set substantially above ambient atmospheric pressure, for example to a level of 500 mm Hg. A pressure sensor (or sensors) in the instrument measures the pressure in the blood tubing set. After a predetermined dwell time (e.g., 30 seconds), a second measurement of the pressure is made, and the rate of pressure decay in the blood tubing set is determined.

If the test indicates a pressure decay occurred greater than a predetermined limit, such as 25 mm Hg in 30 seconds, it indicates that there is a failure or leak somewhere in the extracorporeal circuit. The machine may take appropriate action, such as prompting the user to change out the extracorporeal circuit, sounding an alarm, or initiating a service call. A second pressure decay test may also be performed if the first test indicates a failure, in order to confirm the existence of a failure.

A clamp integrity test has been devised to specifically test the integrity of the arterial line pinch clamp and the venous line pinch clamp. In order to perform this test, the extracorporeal circuit includes a vent line incorporating an air pump capable of forcing air into, or removing air from, a first portion of the blood tubing set extending between the arterial line pinch clamp and the venous line pinch clamp, i.e., the portion of the blood tubing set including the blood pump. For example, the vent line of the venous bubble trap may include an air pump that can add or remove air from the venous bubble trap, which has the effect of introducing or removing air from the first portion of the blood tubing set.

The clamp integrity test includes the steps of removing fluid, which may be present in the arterial and venous lines, from the blood tubing set and then closing the arterial and venous pinch clamps. The first portion of the blood tubing set between the arterial pinch clamp and the venous pinch clamp is pressurized to a pressure substantially above atmospheric pressure. Then, a portion of the arterial line between the arterial clamp and the arterial manifold port is vented to ambient pressure (such as by opening a first valve behind the arterial manifold port). A portion of the venous line between the venous clamp and the venous manifold port is also vented to atmospheric pressure (such as by opening a second valve behind the venous manifold port). The result is that the middle or first portion of the blood tubing set is pressurized, with the arterial and venous pinch clamps maintaining the pressurization of the first portion of the blood tubing set.

The pressure in the first portion of the blood tubing set is measured. The test may be performed as a pressure decay test, such that after a dwell period (for example, 30 seconds), a second measurement of pressure is taken and the pressure decay determined. The magnitude of the pressure decay is indicative of the condition of the arterial and venous clamps. In the event of a failure as indicated by a substantial pressure decay, the machine can either go in to an alarm mode, prompt the user of the machine to initiate a service call, or automatically initiate the service call with built-in communications hardware (such as a modem preset to dial into a service bureau or the manufacturer).

In an alternative embodiment of the test, the pinch clamps may relieve pressure until the pressure is at a value low enough for the pinch clamps to maintain the pressure at a certain level. The pinch clamps would be tested by requiring that a pressure of at least a predetermined level must be maintained, for example 400 mm Hg. If the pressure dropped below this level, the pinch clamps would fail the test and the machine would proceed into an alarm mode, prompt the user to take corrective action, or initiate a service call automatically.

A further blood tubing set integrity test is also provided, which is specifically designed to test the connection of the arterial and venous lines to the arterial and venous manifold ports. If the connections are not securely made, or if the arterial connector is inadvertently connected to the venous port and vice versa, this test will detect these conditions and prompt the user to take corrective action.

This test has a first portion, in which vacuum and pressure techniques are used to determine that the connectors are in fact installed on the manifold ports and that the manual clamps installed on the lines themselves have not been inadvertently left closed by the operator. If the blood tubing set pressurizes (due to the closure of valves "downstream" of the disinfection manifold ports, thereby isolating the extracorporeal circuit and allowing it to pressurize and/or due to an occlusive component such as a blood pump) and the pressure decay is minimal or none, the arterial and venous connectors are installed on the manifold ports and locked into place. Similarly, if a vacuum can be drawn upstream of the manifold ports and this vacuum is registered downstream, the arterial and venous line connectors are correctly installed with the manual clamps in the open position.

A second portion of this third test determines whether the arterial and venous lines are installed onto the arterial and venous ports (and not installed incorrectly such that the arterial line is installed on the venous port and vice versa). This portion of the test involves the introduction of a fluid (e.g., water, dialysate, saline, etc.) into one of the arterial or venous lines and sending the fluid out of the port the line is connected to and detecting the presence or absence of the fluid with a suitable means, such as a thermistor downstream of the port. Other possible means for detecting the presence of the fluid can be used, such as pressure, conductivity, or optical sensors. For example, if the fluid was introduced into the venous line and the thermistor downstream of the venous port detects the fluid, then the lines are properly installed. However, if the fluid is introduced into the venous line and the venous thermistor does not detect the fluid or the thermistor downstream of the arterial port detects the fluid, then the lines were installed incorrectly. The user is then prompted to interchange the connection of the arterial and venous lines (or take other action to see that the arterial and venous lines are properly installed). The first and second portions of this test can be performed independently of each other.

These and many other features, advantages and objects of the invention will be more apparent from the following detailed description of presently preferred embodiments of the invention.

BRIEF DESCRIPTION OF THE DRAWINGS

Presently preferred embodiments will be described in detail below in conjunction with the appended drawings, in which like elements refer to like elements in the various views, and in which.

DETAILED DESCRIPTION OF THE PREFERRED EMBODIMENT

Before the preferred embodiments of the extracorporeal circuit integrity tests are described, a brief overview of a presently preferred extracorporeal circuit, disinfection manifold, and dialysate circuit for a representative dialysis machine will be set forth in order to better understand the inventors' best mode known for practicing the invention. To the extent that the extracorporeal circuit, dialysate circuit or disinfection manifold incorporate components that are unrelated or otherwise irrelevant to the present invention, they are omitted from the following discussion for the sake of brevity and clarity. The reader is directed to U.S. Pat. No. 5,591,344, issued to Kenley et al. and assigned to the Assignee of the present invention, and published PCT application no. WO 96/25214, for further details on the representative machine. Both of the above references are fully incorporated by reference herein.

Figure 1:
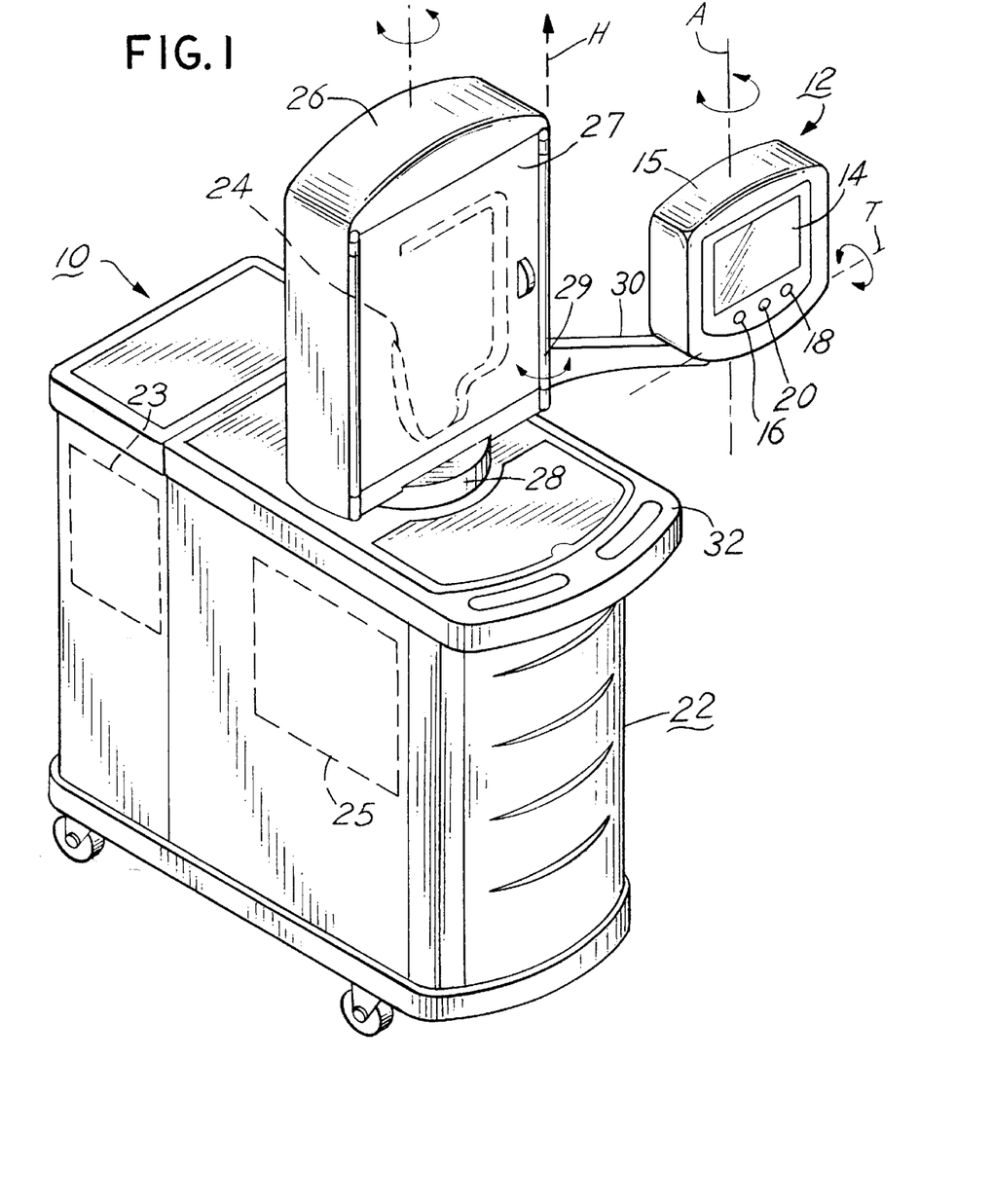
FIG. 1 is a perspective view of a preferred dialysis machine that includes an extracorporeal circuit module on which the integrity tests described herein are performed.

FIG. 1 is an illustration of a dialysis machine 10, having a user interface 12, which may be employed in practicing the invention. The dialysis machine 10 in the illustrated embodiment is suitable for use outside of a traditional dialysis clinic setting, such as the home, nursing home or self-care clinic environment, however the invention is not considered limited to such uses of a machine or the particular machine illustrated. The dialysis machine 10 includes an extracorporeal circuit module 24 mounted above a lower cabinet 22. The extracorporeal circuit is housed behind a door 27 in an enclosure 26 mounted to a turntable 28. The turntable 28 is moveably mounted to the top of the lower cabinet 22 such that the turntable 28, enclosure 26 and extracorporeal circuit module 24 are capable of rotation as a unit relative to the lower cabinet 22 about a vertical axis.

The dialysis machine 10 has a water treatment module 23 and a dialysate preparation module 25 contained within the lower compartment or cabinet 22. The water treatment module 23 plays no part in the present invention, and is described in detail in the '344 patent to Kenley et al. Additionally, the manner in which the dialysate solutions are prepared in the dialysate preparation module 25 and circulated through a dialysate circuit to a dialyzer in the extracorporeal circuit in the enclosure 26 is not particularly important to this invention, and may be as described in the Kenley et al. '344 patent (a preferred embodiment), or otherwise.

The details as to the user interface 12 are also not particularly important insofar as the present invention is concerned, and may be as described in the patent application of Rodney S. Kenley et al., Ser. No. 08/800,405 filed Feb. 14, 1997 or as described in the above-referenced Grogan et al. patent, or otherwise. The user interface includes a touch sensitive display screen 14 and a set of three hard keys 16, 18 and 20 that are pressed by the user to enter and change parameter values and information for the machine. The user interface is connected via a hinge 29 and arm 30 to the cabinet 26. The user interface rotates about a tilt axis T and a vertical axis A so as to enable the user interface to be positioned at a location convenient for the patient. The user interface arm 30 may also be mounted to the front corner 32 of the machine.

Figure 2:
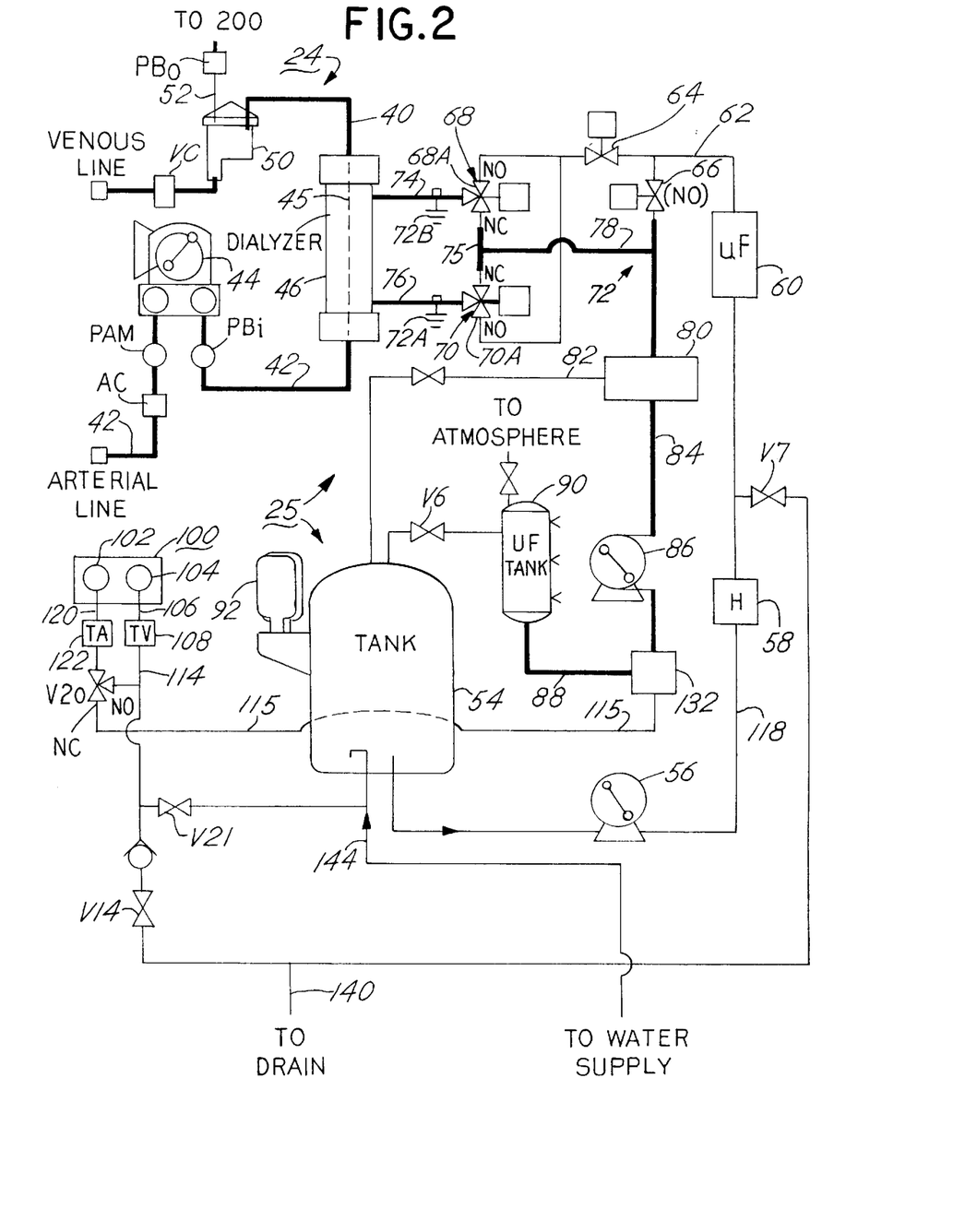
FIG. 2 is a schematic illustration of an extracorporeal circuit and dialysate preparation modules of the dialysis machine of FIG. 1, with components thereof that are not germane to the present invention omitted for the sake of clarity and brevity.

FIG. 2 is a schematic illustration of the extracorporeal circuit 24 and dialysate preparation system 25 of the machine 10 of FIG. 1. In the embodiment of FIG. 2, blood is removed from the patient and introduced into the arterial line 42. The arterial line 42 is threaded through an electrically operable arterial line pinch clamp AC. One or more pressure sensors PA are placed in the line 42 to measure blood and air pressure in the arterial line 42. When the clamp AC is opened and the patient's arterial fistula needle is connected to the connector terminating the arterial line 42, blood is removed from the patient by operation of an occlusive blood pump 44. Blood is circulated to the blood compartment or blood side of a dialyzer 46. Blood-borne toxins and excess water are removed from the blood through the membrane 45 of the dialyzer 46 into a dialysate compartment of dialyzer 46 and into a dialysate circuit 72. The blood is returned to the patient via the venous line 40. A connector (not shown) terminating the venous line connects to a venous fistula needle inserted into the patient. The venous line 40 is threaded through an electrically operable venous line pinch clamp VC.

Figure 3:
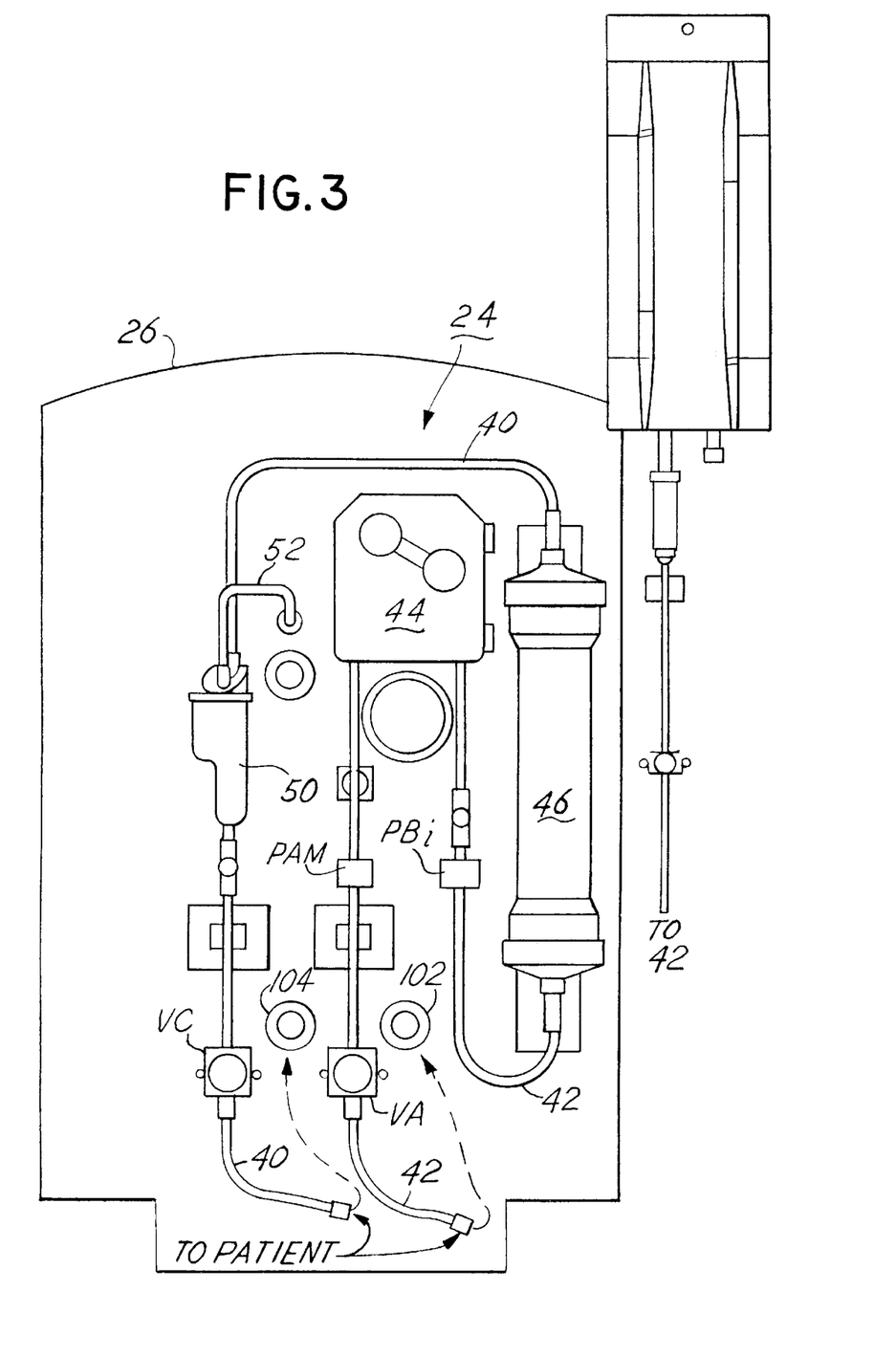
FIG. 3 is an elevational view of the extracorporeal circuit of FIG. 1, indicating that the arterial and venous lines may be connected to respective arterial and venous ports of a disinfection manifold, as they would be when the treatment session is ended and the tests described herein are performed.

To remove air bubbles from the blood being returned to the patient, it is conventional in the dialysis art to place an air trap 50 in the venous line 40. The blood level in the air trap 50 can be adjusted by known and conventional methods, and in FIG. 2 air is pumped into or out of the air trap 50 via a pump 200 (FIG. 4) in line 52 to raise or lower the level in the air trap. Of the circuitry shown in FIG. 2, the dialyzer 46, arterial and venous lines 42 and 40, venous bubble trap 50, blood pump 44, clamps AC and VC and air trap vent line 52 are located in the upper housing or enclosure 26 of FIG. 1, as shown in FIG. 3.

Further details of the particular extracorporeal circuit illustrated in FIG. 2 are not considered to be pertinent to the operation of the present invention, and can be found in the published PCT application of Kenley et al., publication no. WO 96/25214, or in the '344 Kenley et al. patent.

The dialysate preparation module 25 of FIGS. 1 and 2 includes a fifty liter dialysate tank 54 storing a batch quantity of dialysate solution, and a pump 56 for pumping the solution from the tank through a heater assembly 58, a sterile ultrafilter 60, and into a line 62 leading to the dialysate side of the dialyzer 46. An inlet valve 64, bypass valve 66 and first and second inlet and outlet three way valves 68 and 70 are provided in the dialysate circuit 72. The dialysate circuit 72 includes an inlet line 74 and an outlet line 76 from the dialyzer. The outlet line 76 is connected via valve 70 to a dialysate outlet line 78 that leads to a manifold 80. Valves downstream of the manifold 80 dictate whether the returning dialysate is directed to the tank 54 via line 82, or sent via line 84 to an ultrafiltration pump 86. The ultrafiltration pump 86 operates to remove precise volumes of dialysate solution from the dialysate circuit 72 into an ultrafiltration tank 90 via line 88. During the dialysis session, the fluid removed from the patient is pumped by the ultrafiltration pump 86 from the dialysate circuit 72 into the ultrafiltration tank 90, enabling precise measurement of the volume of fluid removed from the patient.

In the illustrated embodiment, dialysate solution is prepared in the tank 54 as a result of mixing chemicals from batch quantity vessels 92 that are introduced into the tank 54 with reverse osmosis water from the water preparation module 23 of FIG. 1. The details are not considered pertinent and are described in the above-referenced Kenley et al. '344 patent. The particular details as to the dialysate preparation module 25, and the manner in which the dialysate solution is prepared and circulated, are not considered to be a part of the invention and can be by any of several other known methods, such as using proportioning systems, or otherwise.

The extracorporeal circuit module 24, positioned inside the upper enclosure 26 of FIG. 1, also includes a disinfection manifold 100 consisting of an arterial line port 102 and a venous line port 104. The disinfection manifold 100 is shown schematically in FIG. 2. The arterial line port 102 receives a patient connector terminating the arterial line 42 after the treatment session is ended. The venous line port 104 receives a patient connector terminating the venous line 40. A preferred construction of the ports 102 and 104, as well as the preferred construction of the patient connectors that terminate the arterial and venous lines, are described in the Kenley et al. '344 patent, therefore a detailed discussion will be omitted. It will be appreciated that the invention can be practiced with other configurations of the ports and patient connectors.

The disinfection manifold 100 is built into the bulkhead inside of the extracorporeal circuit housing or enclosure 26 of FIG. 1, such that the arterial and venous ports 102 and 104 are conveniently exposed to the patient. See FIG. 3. On the back side of the bulkhead, fluid circuitry is provided to place the disinfection manifold ports 102 and 104 in fluid communication with a source of disinfection fluids (such as hot water).

In particular, the arterial port 102 is connected to a line 120 that leads to a thermistor 122 (or TA for Thermistor Arterial), the purpose of which is described below. The thermistor 122 senses the temperature of fluid in line 120 and sends temperature readings to the computer control system for the machine. The thermistor 122 is installed in a line connected to a three-way valve V20, as shown in FIG. 2. When the normally closed port NC of valve V20 is open the line 115 allows fluid to pass from the manifold 132, through the thermistor 122 through the line 120 and into the arterial line 42. Fluid in line 114 can be directed to drain by keeping valve V20 open and opening a valve V14, sending fluid into a drain line 140 when valve V7 is closed.

The venous disinfection manifold port 104 is also connected to the dialysate preparation module 25 via a line 106, venous thermistor 108, and line 114. The line 114 connects to a tee junction. One portion of the tee junction connects to a three-way valve V21 leading to the tank 54. The other portion of the tee connects to a valve V14 which leads either to drain or to a valve V7 and the line between the heater 58 and the ultrafilter 60.

When valves V20, V14 and V21 are closed, the arterial line and venous line are isolated from the rest of the fluid circuitry in the dialysate preparation system. When valves V14, V21 are closed, the NO port of valve V20 allows fluid to recirculate between the lines 106 and 120. Valve V20, V14 and V21 also control the ability of fluid to be introduced into the extracorporeal circuit from the dialysate preparation system and also withdrawn from the extracorporeal circuit and directed to suitable structures or fluid networks, including the dialysate tank 54, the UF tank, or drain.

FIG. 3 is an elevational view of the extracorporeal circuit of FIG. 1, showing the arterial and venous lines 42 and 40, respectively, and how they connect to their respective arterial and venous ports 102 and 104 of the disinfection manifold 100, as they would be when the tests described herein are performed.

Extracorporeal Circuit Integrity Tests

The extracorporeal circuit integrity tests are preferably performed as a series of discrete tests. While they may be performed in any order, it has been found advantageous to perform them in the following order: 1) a dialyzer filter integrity test, 2) a blood tubing set integrity test, and 3) a blood tubing set clamp integrity test. An additional set of tests, to determine that the arterial and venous lines are securely connected to their respective disinfection manifold ports, is also performed (see TEST 4 below). This last set of tests is preferably conducted immediately after the patient reconnects the arterial and venous lines to the extracorporeal circuit disinfection manifold ports, and before the other three tests, although it too could be formed in a different sequence. For example, this last test could be conducted with the extracorporeal tubing set is replaced.

TEST 1 Dialyzer Integrity Test

Initial Conditions:

The patient has reconnected the arterial 42 and venous lines 40 to the disinfection manifold ports 102 and 104 of the disinfection manifold 100. The disinfection cycle for the dialysate preparation module 25 and the extracorporeal circuit 24 (such as a hot water disinfection cycle) has been performed. The extracorporeal circuit 24 is filled with reverse osmosis (RO) filtered water. The dialysate circuit 25 is at ambient pressure.

Test procedure:

1. The pinch clamp VC through which the venous line 40 is threaded is closed.
2. The air pump 200 (FIGS. 4 and 5) in the venous bubble trap vent line 52 is operated to pump air into the air trap line 52. The occlusive blood pump 44 prevents RO water from flowing past the blood pump 44, therefore water in the extracorporeal circuit is pushed through the dialyzer membrane 45 into the dialysate circuit 72 (which is open to atmosphere) due to the pressure gradient at the dialyzer membrane 45. Alternatively, fluid from the dialyzer could be pumped by the blood pump 44 to drain via line 114.

3. The venous line 40 upstream of the bubble trap 50 is pressurized to 500 mm Hg with the air pump 200 in the bubble trap vent line 52. The pressure is allowed to stabilize. (The tests described herein that are based on pressurization of the extracorporeal circuit preferably include a pressure stabilization time to insure that the extracorporeal circuit is actually pressurized in a static state.)

4. After the stabilization of the pressure, a pressure reading is taken automatically with the pressure sensor in the air trap vent line (PBo), and the value is stored in a memory for the computer control system governing operation of the machine.

5. Wait for a predetermined dwell period (e.g., 30 seconds) and read the pressure with pressure sensor PBo again. A minimum time of 30 seconds is recommended for the dwell period, with any additional time used for pressure stabilization.

6. If the pressure decay measured by PBo is greater than a predetermined limit (e.g., 25 mm Hg/30 sec), repeat steps 3–5. If the second test indicates pressure decay greater than the limit, replace the extracorporeal tubing set 40, 42 and dialyzer 46 or sound an alarm. If the second test does not indicate a pressure decay greater than the limit, the normal sequence of events are continued and the blood tubing set and dialyzer are not replaced.

TEST 2 Blood Tubing Set Integrity Test

A method is provided for in situ testing the integrity of a blood tubing set for an extracorporeal circuit. Preferably, this test is conducted immediately after test no. 1. As noted above, this test takes advantage of the disinfection manifold ports 102 and 104, which are connected to hydraulic circuitry in the machine by the valves V20, V14, V21 located on the other side of the disinfection manifold 100. As noted above, when the valves V20, V14, V21 are closed, the tubing set 40, 42 is isolated from the rest of the hydraulic circuitry, allowing the extracorporeal circuit to pressurize.

The principle of operation of the test consists of the following steps:

a) The arterial and venous lines 42 and 40 are connected to the respective arterial and venous manifold ports 102 and 104.

b) Fluid which may be present in the blood tubing set is evacuated, by means of opening said arterial and venous clamps AC and VC and introducing air into the arterial and venous lines 42 and 40 to push the fluid out of the extracorporeal circuit via the disinfection manifold ports 102 and 104.

c) The blood tubing set 40, 42 is then isolated from the hydraulic circuitry in the machine by closing the valves V20, V14 and V21.

d) Air is forced into the blood tubing set (such as by operating the pump 200 in the line 52, see FIG. 4) so as to raise the pressure in the blood tubing set 40, 42 substantially above ambient atmospheric pressure.

e) The pressure in the blood tubing set is measured with a pressure sensor, such as pressure sensor PBo in the line 52 (FIG. 2).

f) The pressure decay in the blood tubing set is determined by making a second pressure measurement after a predetermined dwell period has elapsed, with the magnitude of the pressure decay indicative of the condition of the blood tubing set. For example, if the pressure remains substantially constant after the dwell period, the blood tubing set 40 and 42 and associated connections to hardware are deemed to be in a satisfactory condition. However, if the pressure decay is too great, the tubing set is deemed to have failed and the user is prompted to replace the entire blood tubing set and dialyzer.

In a preferred embodiment of the test, the arterial and venous manifold ports receiving the arterial and venous lines are installed in the dialysis machine such that they are in fluid communication with a dialysate preparation system. This is the case in the embodiment of FIG. 2. When the valves V14, V20, V21 are closed, they isolate the ports 102 and 104 from the dialysate preparation system. Additionally, the preferred design is such that when the valves are open they allow fluid to be directed into the extracorporeal circuit from the dialysate preparation system. Such fluids may include dialysate solution, water, or a disinfection fluid such as heated water or a heated citric acid solution. Alternatively, fluid may be directed into the extracorporeal circuit through the dialyzer membrane using a pump such as dialysate pump 56 or ultrafiltration pump 86.

A presently preferred implementation of the test is as follows:

Initial Conditions:

The arterial and venous lines are still connected to their respective ports in the disinfection manifold 100. The portion of the blood tubing set from the air trap 50 (including the dialyzer 46) to the blood pump 44 is pressurized to approximately 500 mm Hg.. The portion of the blood tubing set from the air trap 50 (including the blood line clamps) to the blood pump 44 has some water in the line. The venous clamp VC is closed (set to not allow flow through the venous line).

1. With port NO of valve V20 open, V14 closed, and valve V21 open, the clamp AC in the arterial line 42 is opened, and the air pump in line 52 and blood pump 44 are run for a short duration to push any residual water from the arterial line 42 through the port 102 and into the dialysate circuit 72 and tank 54.

2. The clamp VC in the venous line 40 is opened and the air pump in line 52 is run to send any residual water in the venous line 40 to the dialysate circuit via valve V21.

3. Leave the clamps open (such that fluid can pass through the lines 40, 42) and close all valves to atmosphere (V14, V21, V20). Continue to push air into the extracorporeal circuit 24 with the air pump 200 in the venous trap vent line 52 until the blood tubing set pressure is approximately 500 mm Hg as measured by the pressure sensor Pbi in the arterial line.

4. Allow the pressure in the blood tubing 40, 42 set to stabilize. Then read the pressure with the pressure sensor in the venous bubble trap vent line PBo and store the value in the system memory.

5. Wait for a dwell period of 30 seconds, and read the pressure again using PBo.

6. If the pressure decay is greater than a predetermined limit (25 mm Hg/30 sec), repeat steps 3–5. If a second test indicates pressure decay greater than the limit, replace extracorporeal circuit tubing set 40, 42 and dialyzer 46 or sound alarm. If the second test does not indicate a pressure decay greater than a limit, continue with normal sequence of events and do not replace extracorporeal tubing set and dialyzer.

In a preferred embodiment, the computer control system that controls the pressurization of the blood tubing set stores information as to the particular commercial dialyzer that is being used, and a table relating commercial dialyzers with a maximum value of trans-membrane pressure (TMP) specified by the manufacturer for the dialyzer. The information as to the dialyzer currently installed on the machine may be input into the computer system via the user interface 12 by the user at the time the extracorporeal circuit is installed (i.e., when the machine is new) or at the time the dialyzer and blood tubing set are replaced. The computer control system causes the blood tubing set to be pressurized to a predetermined value associated with the particular dialyzer installed on the machine. This is because the test should be conducted at a pressure in the blood tubing set that is below this maximum TMP value for the particular dialyzer installed in the machine.

Test No. 3 Blood Line Clamp Test

Initial Conditions:

The arterial and venous lines are still connected to the disinfection manifold 100. The entire blood tubing set 40, 42 and dialyzer 46 (including the portion between the arterial clamp AC and the blood pump 44) are pressurized to approximately 500 mm Hg., unless test no. 2 failed. The blood line clamps VC and AC are open, thereby allowing fluid to pass through the clamps. The UF tank is vented to atmosphere.

1. Close both arterial and venous blood line clamps AC and VC.
2. Vent the arterial line 42 from the arterial clamp AC past the disinfection manifold port 102 and to the UF tank and therefore to atmosphere by turning on port NC of V20.
3. Vent the venous line 40 from the venous clamp VC past the disinfection manifold port 104 and to the dialysate tank 54, and therefore to atmosphere, by turning on valve V21 (valves venting the tank 54 and UF tank 90 are already open).
4. Measure the pressure in the two portions of the extracorporeal circuit on both sides of the blood pump between the clamps with the pressure sensor in the arterial line (PAM) and the pressure sensor in the air trap vent line (PBo). Note that since the portion of the extracorporeal circuit between the arterial and venous clamps was already pressurized at the start of the test, there is no need for a stabilization time prior to taking the pressure measurements.
5. Measure the pressures again after a 30 second delay and calculate the rate of decay. If either rate of decay is greater then the pre-set limit (e.g., 25 mm Hg/30 seconds), then trigger an alarm for service repair (i.e., the clamps AC and or VC need to be replaced). Alternatively, the user interface 12 may display a message on the screen 14 prompting the user to ensure that the lines are correctly placed in the arterial and venous clamps.

Note also that if the blood pump were not occlusive, only one pressure sensor need be used in the portion of the extracorporeal circuit between the clamps.

In an alternative embodiment to this test, step 5 would not be performed, but rather the pressure would be continuously monitored to see if the pressure decay stabilizes above a predetermined threshold limit. For example, if the pressure drops from the initial pressure level (say, of 550 mm Hg) to 450 mm Hg, but remains constant at that pressure thereafter, and if it has previously been determined that maintenance of pressure at or above 400 mm Hg indicates that the clamps meet patient safety requirements, then the clamps will have been deemed to have passed the test. However, if the tubing set was pressurized to say 550 mm Hg and decayed to 380 mm Hg and stabilized there, then the clamps will have been deemed to have failed.

In the above alternative embodiment, the pressure stabilization level used for the test will depend on many factors, such as the level of acceptable back pressure designed into the extracorporeal circuit, the type of clamp and tubing that are used in the extracorporeal circuit, and the level of clamp performance that the manufacturer is willing to tolerate as acceptable.

It will also be apparent from the above description that the clamp test can be done on the arterial and venous lines at the same time, or serially one after the other. Further, the test could be performed without having the connectors terminating the arterial and venous lines plugged into the disinfection manifold, as long as the portion of the blood lines on the patient side of the clamps is at a substantially different pressure from the portion on the blood pump and dialyzer side of the clamps. What is important is that the portion of the blood tubing set on one side of the clamp is pressurized relative to the other side of the clamp, and the pressure is monitored to determine the condition of the clamp. This is accomplished by either a pressure decay type of test or a pressure maintenance type of test as set forth above.

Test No. 4 Arterial and Venous Line Connection to Manifold Port Test

This test provides a method for verifying the proper connection of the arterial and venous lines 42 and 40 the arterial and venous manifold ports. The test is performed after the user has reconnected the arterial and venous lines 42 and 40 to the arterial and venous disinfection manifold ports. It can also be performed when a new tubing set is installed on the machine. The test may be performed immediately after the above three tests have been performed, or earlier, such as immediately after the patient has reconnected the arterial and venous lines to the ports of the disinfection manifold at the end of a dialysis treatment.

A preferred embodiment of the test includes two separate procedures or sub-tests: (1) an air pressure test to verify that the connections between the arterial and venous lines to the ports have been made, and (2) a test with fluid to determine that the arterial and venous lines have been connected to their respective arterial and venous ports, and not the otherwise (i.e., the arterial line is incorrectly installed on the venous port). As an initial condition, the arterial and venous clamps AC and VC are in an open condition.

The first sub-test (the air pressure test) includes the following steps in a preferred embodiment:

(1) The valves V14, V21 and V20 downstream of the disinfection manifold ports 102 and 104 are closed to isolate the arterial and venous lines 42 and 40.

(2) Next, air present in the arterial and venous lines is removed by running the air pump 200 in the venous bubble trap vent line 52 in the reverse direction to draw the air out of the lines 40 and 42, through the bubble trap 50 and out line 52. Since the blood pump 44 in the extracorporeal circuit is occlusive, if a reduction in pressure or vacuum is detected with a pressure sensor PAM in the arterial line, it indicates that the arterial and venous lines were installed on the arterial and venous ports 102 and 104 and that the arterial and venous clamps AC and VC are in an open condition.

(3) Next, air is pumped into the arterial and venous lines with the air pump 200 in line 52 to pressurize the blood tubing set 40, 42 to a predetermined value (e.g., 500 mm Hg). The pressure is again measured with the pressure sensor PAM in the arterial line. The pressure decay is then measured. If the pressure is maintained in the inlet to the blood pump 44, it indicates that the connectors terminating the arterial and venous lines have been securely locked to the arterial and venous manifold ports 102 and 104. For example, and with reference to the preferred embodiment of the manifold ports shown in the Kenley et al. '344 patent, the maintenance of pressure indicates that the quarter turn of the manifold knob on the port has been done to lock the arterial connector to the port, resulting in a tight seal between the 0-ring in the port to the shoulder sealing surface of the connector.

Figure 4:
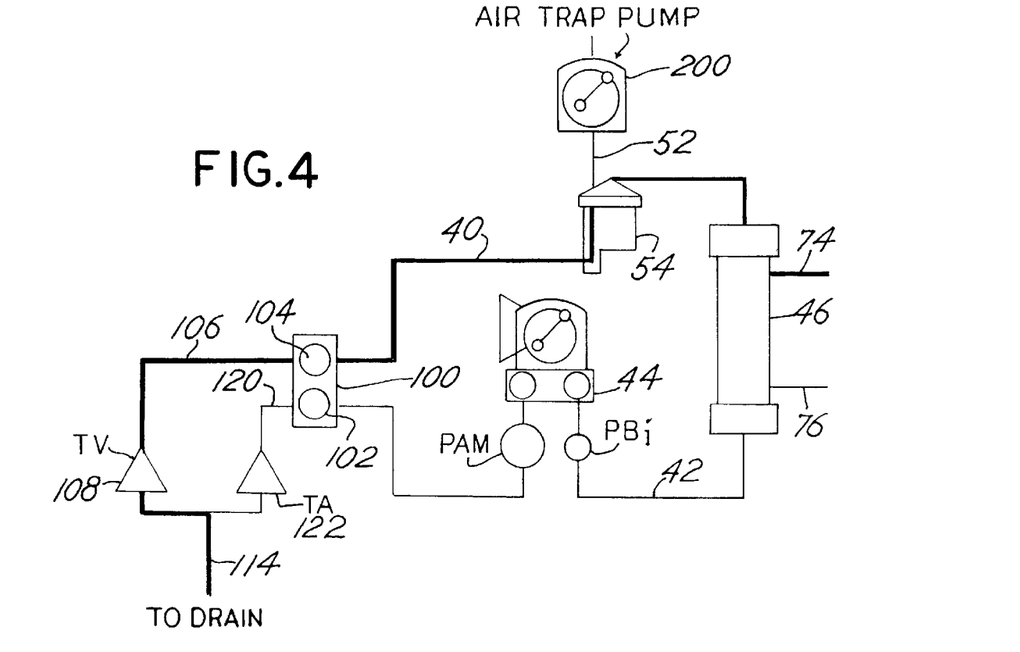
FIG. 4 is a simplified schematic diagram of the extracorporeal circuit of FIG. 2 and thermistors positioned downstream of the disinfection manifold, showing the path of heated fluid that is used to test whether the arterial and venous lines have been correctly installed in the disinfection manifold ports.
Figure 5:
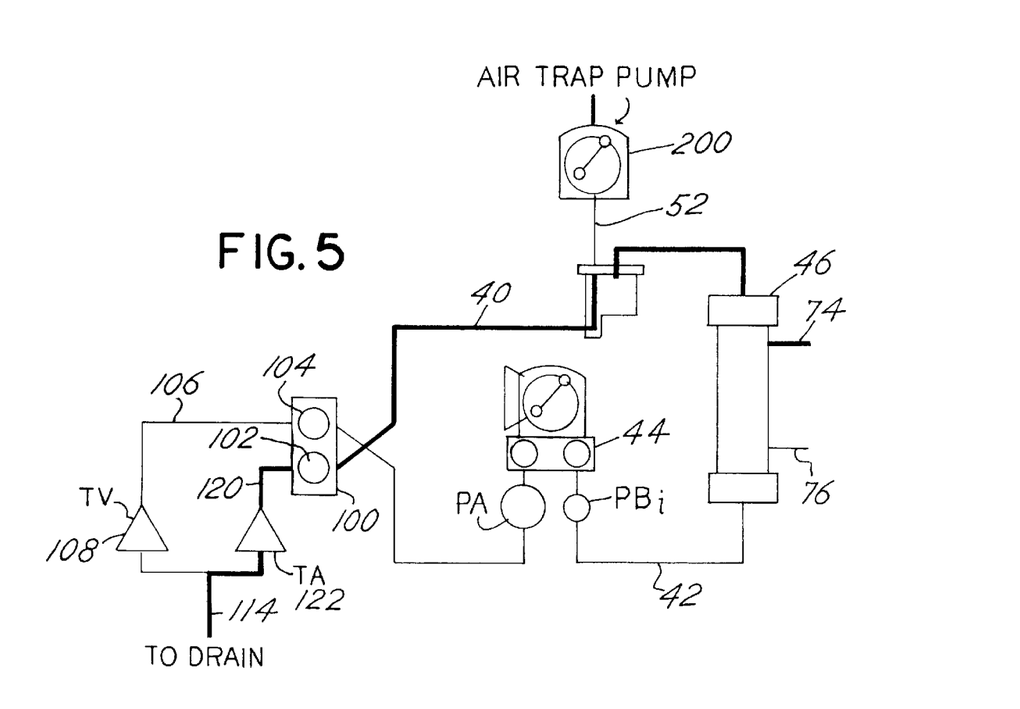
FIG. 5 is simplified schematic diagram of the extracorporeal circuit of FIG. 2 and thermistors positioned downstream of the disinfection manifold, showing the path of heated fluid when the arterial and venous lines have been incorrectly installed in the disinfection manifold ports.

The second part of the test is then performed to determine that the arterial line 42 and respective connector is locked to the arterial port 102 and the venous line 40 and associated connector is locked to the venous port 104. With reference to FIGS. 2, 4 and 5, this test takes advantage of a fluid detection device positioned downstream of at least one of the arterial or venous ports of the disinfection manifold. In the illustrated embodiment, two thermistors TA (122) and TV (108) are placed in the fluid lines 120 and 106 behind the disinfection manifold ports 102 and 104.

In this test, a heated fluid (or, equivalently, a fluid at any given temperature) is introduced into one of the arterial and venous lines, and the fluid is directed out of the manifold port that the line receiving the fluid is connected to. The fluid is detected by suitable fluid detection equipment, such as the thermistors TA or TV downstream of the disinfection manifold ports. If the fluid is introduced into the venous line, then the thermistor downstream of the venous disinfection manifold port, TV, will sense the fluid, indicating that the venous and arterial lines were correctly installed in their associated ports. Conversely, if the thermistor in the line downstream of the arterial port TA detects the fluid, and/or if the thermistor downstream of the venous port fails to detect the fluid, then it indicates that the lines were incorrectly installed: i.e., the venous and arterial lines were installed on the wrong ports. The user is then prompted to take corrective action, such as switching the connection of the arterial and venous lines.

It will thus be appreciated that the invention will work with only one thermistor (such as thermistor TV), and that thermistor TA may be dispensed with. In particular, if the fluid is introduced into the venous line and the venous thermistor TV does not send a signal to the computer control system indicating the detection of the fluid, then it is assumed that the arterial and venous lines are not installed correctly. In this respect, the absence of a signal, a null signal from the venous thermistor TV, or a signal indicating ambient temperature when heated fluid is introduced into the venous line, all would indicate that the lines were installed incorrectly. Of course, if a different type of fluid detection device is used (such as a conductivity or pressure sensor) only one such device need be used.

In the preferred embodiment, the fluid used in this test is water. The water is introduced into the venous line 40 by backfiltering heated water (e.g., water at 50 degrees C.) from the dialysate side of the dialyzer membrane 45 into the extracorporeal circuit 24. The blood pump 44 is turned off, and its occlusive nature requires that the backfiltered heated water flow through the venous line 40. As the fluid exits the venous line 40 and flows through the venous manifold port 104, it passes into the line 106 containing the "venous" thermistor TV. The thermistor TV detects the 50 degrees C. fluid, and responsively sends a signal indicating the temperature of the fluid to the central computer control system for the machine. The computer control system now has confirmation that the arterial and venous lines are properly installed. This connection is illustrated in the simplified schematic diagram of FIG. 4. Any other convenient fluid such as dialysate solution, saline solution, or a cleaning solution could be used.

Additionally, the invention can be employed with other types of fluid sensing equipment, such as ultrasonic, conductivity, pressure, optical, or other types of sensing or detecting equipment. Thermistors are used in the preferred embodiment because they are also used in other aspects of machine operation (such as monitoring the temperature of hot water during a hot water disinfection cycle). In a machine that uses a chemical disinfection system, then conductivity, optical, or chemical sensors could be used.

Note that in the illustrated embodiment an occlusive blood pump is used, thereby forcing the fluid into the venous line. This dictates that the fluid detection device be installed downstream of the venous port. If a non-occlusive blood pump is used, then the arterial clamp may be closed, resulting in the fluid being forced into the venous line. Alternatively, of course, the venous clamp could be closed thereby forcing the fluid past the non-occlusive blood pump into the arterial line and out the arterial manifold port, in which case the fluid detection device would be positioned in the line downstream of the arterial manifold port. A similar result could be obtained by closing the venous clamp and reversing the blood pump.

FIG. 5 is simplified schematic diagram of the extracorporeal circuit and thermistors TA and TV positioned downstream of the disinfection manifold 100, showing the path of heated fluid when the arterial and venous lines have been incorrectly installed in the disinfection manifold ports. If the thermistor TA registers the presence of the hot fluid introduced into the venous line 40, then the patient has installed the arterial and venous lines on the wrong ports. The central computer system prompts the user to interchange the connections of the arterial and venous lines 42 and 40 relative to the ports 102 and 104. If neither of the thermistors TA and TV detect the fluid, then other corrective action is taken, such as prompting the user to initiate a service call, install the arterial or venous line connectors to the ports, etc.

An alternative method of determining whether the arterial and venous line connectors are correctly installed on their respective arterial and venous ports of the disinfection manifold will be described in conjunction with FIGS. 6 and 7. This method involves placing the extracorporeal circuit at a different pressure from the hydraulic circuit on the other side of the disinfection manifold, and then opening a valve on the other side of the disinfection manifold to see whether a change in pressure occurs in the correct side of the occlusive blood pump in the extracorporeal circuit. For example, if the valve downstream of the venous port is opened and the pressure sensor in the venous portion of the extracorporeal circuit detects a change in pressure, then the venous line is correctly installed on the disinfection manifold. Conversely, if the pressure change is not detected in the venous portion of the extracorporeal circuit, then the arterial and venous lines are installed on the wrong ports.

Figure 6:
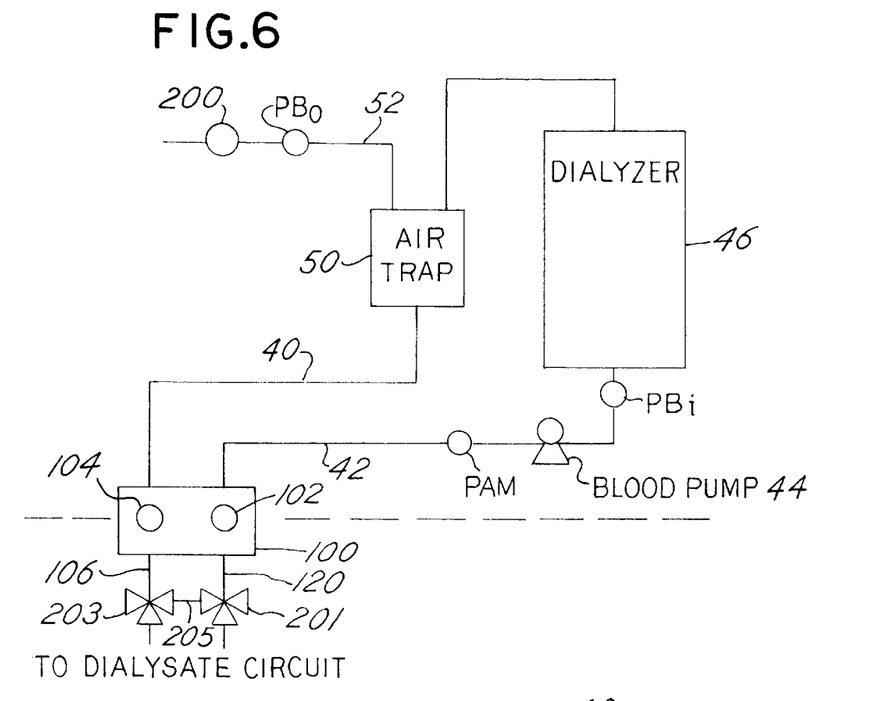
FIG. 6 is a simplified schematic diagram of the extracorporeal circuit of FIG. 2 showing the apparatus used for conducting a pressure test to determine whether the arterial and venous lines have been correctly connected to the disinfection manifold ports.

Referring now in particular to FIG. 6, the arterial and venous lines 42 and 40 are shown connected to their respective arterial and venous ports 102 and 104. The valves 201 and 203 downstream of the arterial and venous ports in lines 120 and 106 are closed, thereby isolating the extracorporeal circuit from the hydraulic circuitry on the other side of the valves 201 and 203. The blood pump 44 is occlusive. Therefore, when the air pump 200 is operated to pressurize the extracorporeal circuit (or, equivalently, draw a vacuum in the extracorporeal circuit), the portion of the extracorporeal circuit downstream of the blood pump 44, including the dialyzer 46, air trap and venous line is pressurized to a desired pressure. The conduit linking valves 201 and 203 is open, allowing the arterial line 42 up to the blood pump to also pressurize. The pressure sensor PBo measures the pressure in the venous portion of the extracorporeal circuit. The pressure sensor PAM measures the pressurization of the arterial portion of the extracorporeal circuit.

The line 205 linking valves 201 and 203 is closed off, with the arterial and venous lines thereby isolated from each other and from the hydraulic circuitry on the other side of the valves 201 and 203. At this point, the valve 203 is opened, releasing pressure in the line that is connected to the port 104 (venous line 40 in FIG. 6). If the lines are installed correctly, pressure sensor PBo should immediately detect the change of pressure. When PBo sends a signal to the computer control system that this pressure change occurred, the lines are determined to be correctly installed. Additionally, since the arterial line 42 is also pressurized, and valve 201 remains closed, the pressure measured by PAM should not change. This provides a backup or redundant check that the lines are correctly installed.

Figure 7:
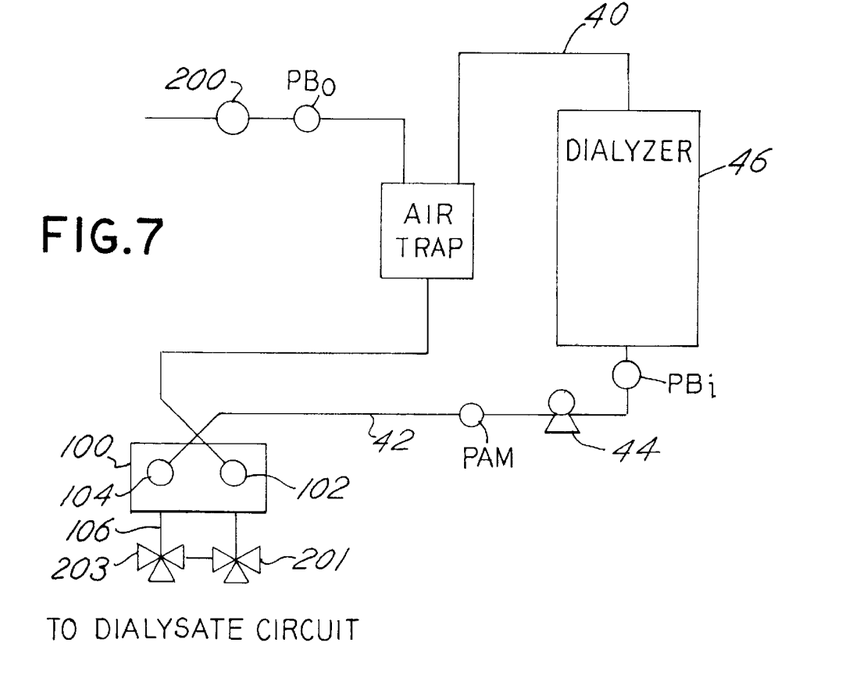
FIG. 7 is a schematic diagram of the extracorporeal circuit of FIG. 6 with the lines connected to the wrong ports in the disinfection manifold.

FIG. 7 illustrates the situation in which the lines 40 and 42 are incorrectly installed on the wrong ports. When valve 203 is opened, the pressure change is detected in PAM, and not in PBo. This will result in an alarm signal being generated in the machine, or a display of a prompt to the user to check the blood tubing set connections.

As noted above, it makes no difference whether a vacuum is drawn on the extracorporeal circuit or whether a higher pressure is generated in the extracorporeal circuit. The key is that the pressure in the arterial and venous lines is different from the pressure in the lines on the other side of the valves 201 and 203. While in the above example, the pressure differential is generated by maintaining the lines connected to the dialysate circuit at substantially atmospheric pressure and using the pump 200 to create the pressure differential, it would also be possible to maintain the extracorporeal circuit at any given pressure (e.g., atmospheric), and create either higher or lower pressure in both of the lines on the other side of the valves 201 and 203. When one of the valves 201 or 203 is opened, the pressure change will be detected by the pressure sensors PBo or PAM. As in the case of FIG. 6, when the valve 203 is opened, the pressure change should be detected in PBo to indicate that the lines are correctly installed.

Presently preferred embodiments of the invention have been set forth herein. Persons of skill in the art will appreciate that various modifications to the preferred embodiments set forth above may be made, without departure from the true spirit and scope of the invention. Examples of such modifications include the design of the extracorporeal circuit or dialysate circuit (as such details tend to be unique to the particular dialysis machine the invention is practiced in), the construction of the manifold ports and patient connectors, and the particular manner by which the arterial and venous lines are coupled to hydraulic circuitry within the machine. Further, while some of the tests described herein involve generation of super-atmospheric pressure in the blood tubing set and measurement of pressure decay, generation of vacuum or below atmospheric pressure within the blood tubing set and measuring an increase in pressure is considered equivalent to the disclosed techniques. As noted previously, alternative and known methods of fluid detection may be employed besides thermistors. This true spirit and scope of the invention is determined by the appended claims, to be interpreted in light of the foregoing specification.

What is claimed is:

1. A method for testing the integrity of a blood tubing set for an extracorporeal circuit, said blood tubing set comprising an arterial line with an arterial clamp and a venous line with a venous clamp, the method performed in situ in a machine containing said blood tubing set and having arterial and venous manifold ports for receiving said arterial and venous lines, said ports connected to hydraulic circuitry in said machine by one or more valves, the method comprising the steps of:
   a) connecting said arterial and venous lines to said arterial and venous manifold ports;
   b) evacuating fluid which may be present in said blood tubing set, comprising the steps of opening said arterial and venous clamps and introducing air into said arterial and venous lines to push said fluid out of said extracorporeal circuit;
   c) isolating said blood tubing set from said hydraulic circuitry in said machine by closing said one or more valves;
   d) forcing air into said blood tubing set so as to raise the pressure in said blood tubing set substantially above ambient atmospheric pressure;
   e) measuring the pressure in said blood tubing set with a pressure sensor; and
   f) measuring the pressure decay in said blood tubing set by making a second pressure measurement after a dwell period, the magnitude of said pressure decay indicative of the condition of said blood tubing set; and wherein said arterial and venous manifold ports receiving said arterial and venous lines are in fluid communication with a dialysate preparation system and wherein said one or more valves, when closed, isolate said ports from said dialysate preparation system.

2. The method of claim 1, wherein said extracorporeal circuit is incorporated in a machine for treating a patient suffering from inadequate kidney or liver function.

3. The method of claim 1, wherein said dwell period comprises between about 20 and about 30 seconds.

4. The method of claim 2, where said machine further comprises a dialyzer and a computer control system controlling the pressurization of said blood tubing set, and wherein said computer control system operates an air pump connected to said blood tubing set so as to pressurize said blood tubing set to a predetermined value associated with a particular commercial source of said dialyzer.

5. A method for testing the integrity of an arterial line clamp and a venous line clamp of a machine having a blood tubing set, said blood tubing set comprising an arterial line threaded through said arterial line clamp, a venous line threaded through said venous line clamp, and a vent line incorporating an air pump capable of forcing air into or removing air from a first portion of said blood tubing set extending between said arterial line clamp and said venous line clamp;

the method performed in situ in a machine containing said blood tubing set, the machine comprising arterial and venous manifold ports for receiving said arterial and venous lines, said ports connected to hydraulic circuitry in said machine by one or more valves, the method comprising the steps of:
   a) closing said arterial and venous clamps;
   b) pressurizing said first portion of said blood tubing set between said arterial clamp and said venous clamp to a pressure substantially above atmospheric pressure;
   c) venting a portion of said arterial line between said arterial clamp and said arterial manifold port to ambient pressure;

d) venting a portion of said venous line between said venous clamp and said venous manifold port to atmospheric pressure;

e) measuring the pressure in said first portion of said blood tubing set after said step of venting; and f) determining from said measurements of pressure the condition of said arterial and venous clamps.

6. The method of claim 5, wherein said machine comprises a machine for treating a patient suffering from inadequate kidney or liver function.

7. The method of claim 5, wherein said step of measuring pressure comprises the step of measuring a level at which the pressure in said first portion of said blood tubing set stabilizes after said step of venting has been completed, wherein said clamps are deemed to have failed if said level is lower than a predetermined threshold level.

8. The method of claim 5, wherein said step of measuring pressure comprises the step of measuring the pressure decay in said first portion of the extracorporeal circuit for a predetermined dwell period.

9. The method of claim 6, where said machine further comprises a dialyzer and a computer control system controlling the pressurization of said blood tubing set, and wherein said computer control system operates an air pump in communication with said blood tubing set to pressurize said blood tubing set to a predetermined value associated with a particular commercial source of said dialyzer.

10. The method of claim 6, wherein said arterial line is vented to atmosphere via an ultrafiltration tank within said machine and wherein said venous line is vented to atmosphere via a dialysate tank within said machine, said ultrafiltration tank and dialysate tanks in fluid communication with said arterial and venous lines via first and second valves and said arterial and venous manifold ports.

11. The method of claim 5, wherein said blood pump is an occlusive pump and said measurements of pressure and pressure decay are taken by first and second pressure sensors located on either side of said blood pump.

12. The method of claim 1, further comprising the additional steps after step f) of repressurizing said blood tubing set to a predetermined value, waiting a second dwell period, and measuring the pressure decay of said blood tubing set a second time, and subsequently prompting a user of said machine to replace said blood tubing set or extracorporeal circuit in the event that said pressure decay again exceeds a predetermined threshold.

13. The method of claim 5, further comprising the step of prompting the user of said machine to initiate a service call for said machine in the event that said measurements of pressure indicate that said arterial and venous lamps are not operating properly.

14. The method of claim 5, wherein said machine is connected via a communication line to a service agency or manufacturer for said machine, and the method further comprising the step of automatically initiating a service call for said machine via said communications line in the event that said pressure decay exceeds a predetermined threshold limit.

15. In a medical instrument having an extracorporeal blood circuit comprising an arterial line with an arterial clamp and a venous line with a venous clamp, said machine having arterial and venous manifold ports for receiving said arterial and venous lines after a treatment session, said ports connected to hydraulic circuitry in said machine by one or more valves, a method for verifying the proper connection of said arterial and venous lines to said arterial and venous manifold ports, comprising the steps of:

closing said one or more valves to isolate said arterial and venous lines from said hydraulic circuitry;

removing air from said arterial and venous lines and detecting a reduction in pressure with a pressure sensor in said extracorporeal circuit, said reduction in pressure indicating that said arterial and venous lines were installed on said arterial and venous ports and said arterial and venous clamps are in an off condition; and pumping air into said arterial and venous lines to pressurize said blood tubing set to a predetermined value and measuring the pressure decay of said blood tubing set, the absence of a substantial pressure decay indicative that said arterial and venous lines have been securely received by said arterial and venous manifold ports.

16. The method of claim 15, further comprising the step of introducing a fluid into one of said arterial and venous lines and detecting the presence or absence of said fluid with a fluid detection means downstream of one of said arterial or venous ports normally associated with the line that said fluid is introduced into.

17. The method of claim 16, wherein said fluid comprises water.

18. The method of claim 16, wherein said fluid detection means comprises a thermistor.

19. The method of claim 18, wherein said fluid comprises a heated fluid.

20. The method of claim 15, wherein said machine further comprises a first fluid detection means downstream of said arterial port and a second fluid detection means downstream of said venous port, and wherein the method further comprises the steps of introducing a fluid into one of said arterial and venous lines of said blood tubing set and directing said fluid out of the port that said one of said arterial and venous lines is connected to, and detecting said fluid with one of said first or second fluid detection means, wherein the detection of said fluid by the fluid detection means downstream of the other of said arterial or venous manifold ports for a line that did not receive said fluid indicates that said arterial and venous lines are incorrectly installed on said arterial and venous manifold ports.

21. The method of claim 16, wherein said machine comprises a dialysis machine and wherein said extracorporeal circuit further comprises a dialyzer connected to said arterial and venous lines and having a dialysate side and a blood side, and wherein said step of introducing a fluid comprises the step of backflushing said fluid from said dialysate side into said blood side of said dialyzer into one of said arterial or venous lines.

22. In a medical instrument having an extracorporeal blood circuit comprising an arterial line and a venous line, said machine having arterial and venous manifold ports for receiving said arterial and venous lines after a treatment session, said machine further comprising a fluid detection means downstream of at least one of said arterial port and said venous port, a method for verifying the proper connection of said arterial and venous lines to said arterial and venous manifold ports, comprising the steps of:

introducing a fluid into one of said arterial and venous lines of said blood tubing set and directing said fluid out of the arterial or venous manifold port that said one of said arterial and venous lines is connected to, and detecting the presence or absence of said fluid with said fluid detection means.

23. The method of claim 22, wherein said machine comprises a dialysis machine and wherein said extracorporeal circuit further comprises a dialyzer connected to said arterial and venous lines and having a dialysate side and a blood side, and wherein said step of introducing said fluid comprises the step of backflushing said fluid from said dialysate side into said blood side of said dialyzer into one of said arterial or venous lines.

24. The method of claim 23, wherein said machine further comprises occlusive blood pump in said arterial line and wherein said fluid is backflushed into said venous line, and wherein said fluid detection means is positioned downstream of said venous manifold port.

25. The method of claim 22, wherein said fluid is selected from the group of fluids consisting of water, dialysate solution, cleaning solution and saline solution.

26. The method of claim 22, wherein said fluid detection means is selected from the group of detectors consisting of conductivity sensors, pressure sensors, thermistors, capacitative sensors, ultrasonic detectors and optical detectors.

27. The method of claim 22, wherein said fluid detection means is positioned downstream of said venous manifold port and wherein a second fluid detection means is incorporated into said instrument downstream of said arterial manifold port.

28. A method of testing the integrity of a clamp for closing off a blood line of an extracorporeal circuit, said blood line having a first portion upstream of said clamp and a second portion downstream of said clamp terminating in a free end adapted to be connected to a patient, comprising the steps of:

placing said clamp in a closed condition, pressurizing said first portion of said blood line to a pressure substantially above the pressure of said second portion of said blood line;

measuring the pressure within said first portion of said blood line with a pressure sensor; and determining from said measuring of pressure the condition of said clamp.

29. The method of claim 28, wherein said step of measuring the pressure comprises the step of measuring a level at which the pressure in said first portion of said blood line stabilizes, wherein said clamp is deemed to have failed if said level is lower than a predetermined threshold level.

30. The method of claim 29, wherein said step of measuring pressure comprises the step of measuring the pressure decay in said first portion of said blood line for a predetermined dwell period.

31. The method of claim 28, wherein said extracorporeal circuit comprises arterial and venous lines and wherein said arterial and venous lines are closed by arterial and venous clamps, and wherein said first portion of said extracorporeal circuit comprises the portion of said extracorporeal circuit between said arterial and venous line clamps, whereby the integrity of both said arterial and venous clamps are tested when said first portion of said extracorporeal circuit is pressurized.

32. In a machine having an extracorporeal circuit comprising an occlusive blood pump and arterial and venous lines terminating in arterial and venous line connectors, said arterial and venous line connectors received in a disinfection manifold port comprising arterial and venous ports for receiving said arterial and venous line connectors, respectively, said arterial and venous ports connected to a hydraulic system via first and second valves normally associated with said arterial and venous ports and arterial and venous lines, respectively, a method of determining whether said arterial and venous lines are correctly installed on said arterial and venous ports and not vice versa, comprising the steps of:

installing said arterial and venous lines on said disinfection manifold ports;

isolating said arterial and venous lines from said hydraulic system connected to arterial and venous manifold ports by closing said first and second valves linking said arterial and venous manifold ports to said hydraulic system;

creating a pressure differential between said arterial and venous lines and said hydraulic system;

opening one of said first and second valves to thereby bring said hydraulic system and the arterial or venous line connected to the port associated with said first or second valve into equilibrium; and detecting a change in pressure in either said first arterial line or said venous line;

whereby the detection of a change in pressure in the line associated with the valve that is opened indicates that the arterial and venous lines are correctly installed on said arterial and venous manifold ports.

33. The method of claim 32, wherein said step of creating a pressure differential comprises the step of pressurizing said venous line to a superatmospheric pressure with an air pump connected to a venous drip chamber installed in said venous line of said extracorporeal circuit.

34. The method of claim 32, wherein said hydraulic system is maintained at atmospheric pressure during said step of creating a pressure differential.

* * * * *